(12) United States Patent
Fujii

(10) Patent No.: US 10,736,617 B2
(45) Date of Patent: Aug. 11, 2020

(54) FORCE TRANSMISSION MECHANISM FOR MEDICAL DEVICE AND MEDICAL DEVICE

(71) Applicant: OLYMPUS CORPORATION, Tokyo (JP)

(72) Inventor: Masahiro Fujii, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 134 days.

(21) Appl. No.: 15/954,704

(22) Filed: Apr. 17, 2018

(65) Prior Publication Data

US 2018/0235589 A1     Aug. 23, 2018

Related U.S. Application Data

(63) Continuation of application No. PCT/JP2015/081068, filed on Nov. 4, 2015.

(51) Int. Cl.
  *A61B 17/00* (2006.01)
  *A61B 17/29* (2006.01)
  (Continued)

(52) U.S. Cl.
  CPC ........ *A61B 17/00234* (2013.01); *A61B 17/29* (2013.01); *A61B 18/1492* (2013.01);
  (Continued)

(58) Field of Classification Search
  CPC ............ A61B 17/29; A61B 2017/2901; A61B 2017/2902; A61B 2017/2903; A61B 34/71

See application file for complete search history.

(56) References Cited

U.S. PATENT DOCUMENTS

| 6,746,443 B1 | 6/2004 | Morley et al. |
| 2006/0219065 A1 | 10/2006 | Jinno et al. |

(Continued)

FOREIGN PATENT DOCUMENTS

| EP | 1707153 A1 | 10/2006 |
| EP | 2881049 A1 | 6/2015 |

(Continued)

OTHER PUBLICATIONS

International Search Report dated Jan. 26, 2016 issued in PCT/JP2015/081068.

*Primary Examiner* — Todd J Scherbel
(74) *Attorney, Agent, or Firm* — Scully, Scott, Murphy & Presser, P.C.

(57) ABSTRACT

A medical-device force transmission mechanism transmitting a force input at the proximal end of an elongated insertion portion inserted into a body and acting along the longitudinal direction of the insertion portion, to a rotation unit supported at the distal end of the insertion portion in a rotatable manner about the longitudinal axis of the insertion portion, the medical-device force transmission mechanism including: a first force transmitting part passing through the insertion portion and transmitting the force to the distal end of the insertion portion; a force converting part disposed at the distal end of the insertion portion and converting the force transmitted by the first force transmitting part into a rotational force; and a second force transmitting part transmitting the rotational force converted by the force converting part to the rotation unit at a different rotational speed.

1 Claim, 4 Drawing Sheets

(51) Int. Cl.
*A61B 34/30* (2016.01)
*A61B 18/14* (2006.01)
*A61B 34/00* (2016.01)

(52) U.S. Cl.
CPC ..... *A61B 34/71* (2016.02); *A61B 2017/00292* (2013.01); *A61B 2017/00367* (2013.01); *A61B 2017/2905* (2013.01); *A61B 2017/2927* (2013.01); *A61B 2017/2929* (2013.01); *A61B 2034/301* (2016.02)

(56) References Cited

U.S. PATENT DOCUMENTS

| | | | |
|---|---|---|---|
| 2008/0039256 A1* | 2/2008 | Jinno | A61B 34/70 |
| | | | 474/148 |
| 2009/0031842 A1* | 2/2009 | Kawai | A61B 17/29 |
| | | | 74/490.01 |
| 2009/0216249 A1 | 8/2009 | Jinno et al. | |
| 2012/0035617 A1* | 2/2012 | Joshi | A61B 17/0218 |
| | | | 606/130 |
| 2015/0142014 A1 | 5/2015 | Hyodo et al. | |

FOREIGN PATENT DOCUMENTS

| | | | |
|---|---|---|---|
| JP | 2006-305717 A | 11/2006 | |
| JP | 2011-255096 A | 12/2011 | |
| JP | 2012-061593 A | 3/2012 | |
| JP | 2014-023821 A | 2/2014 | |

* cited by examiner

US 10,736,617 B2

FORCE TRANSMISSION MECHANISM FOR MEDICAL DEVICE AND MEDICAL DEVICE

CROSS-REFERENCE TO RELATED APPLICATIONS

This is a Continuation Application of International Application No. PCT/JP2015/081068 filed on Nov. 4, 2015. The content of International Application No. PCT/JP2015/081068 is incorporated herein by reference in its entirety.

TECHNICAL FIELD

The present invention relates to a force transmission mechanism for medical-device and a medical device.

BACKGROUND ART

There is a known medical device for quickly and easily performing a cutting procedure for a site in the airway, such as the pharynx (for example, see PTL 1).

In this medical device, a rotational force applied through the operation of a handle provided at the proximal end of a rigid insertion portion is transmitted, by a drive shaft passing through the insertion portion, to external gear at the distal end of the drive shaft, thus rotating, at the distal end of the insertion portion, a rotation unit that is provided with internal gear engaged with the external gear.

CITATION LIST

Patent Literature

{PTL 1} Japanese Unexamined Patent Application, Publication No. 2011-255096

SUMMARY OF INVENTION

According to one aspect, the present disclosure provides a force transmission mechanism for a medical device, which transmits a force that is input at a proximal end of an insertion portion to be inserted into a body to a rotation unit that is supported at a distal end of the insertion portion in a rotatable manner about a longitudinal axis of the insertion portion, the force input at the proximal end being one along the longitudinal direction of the proximal end of the insertion portion, the medical-device force transmission mechanism comprising: a first force transmitting part configured to pass through an inside of the insertion portion and transmit the force to the distal end of the insertion portion; a force converting part that is disposed at the distal end of the insertion portion and configured to convert the force transmitted by the first force transmitting part into a rotational force; and a second force transmitting part configured to transmit the rotational force converted by the force converting part to the rotation unit at a different rotational speed.

Furthermore, according to another aspect, the present disclosure provides a medical device comprising: any one of the above-described force transmission mechanisms for medical-device; the flexible elongated insertion portion; an operation unit that is provided at the proximal end of the insertion portion and with which the force along the longitudinal direction of the insertion portion is input; and the rotation unit that is supported at the distal end of the insertion portion in a rotatable manner about the longitudinal axis of the insertion portion.

DESCRIPTION OF EMBODIMENT

A medical device 1 and a medical-device force transmission mechanism 2 according to one embodiment of the present invention will be described below with reference to the drawings.

Figure 1:
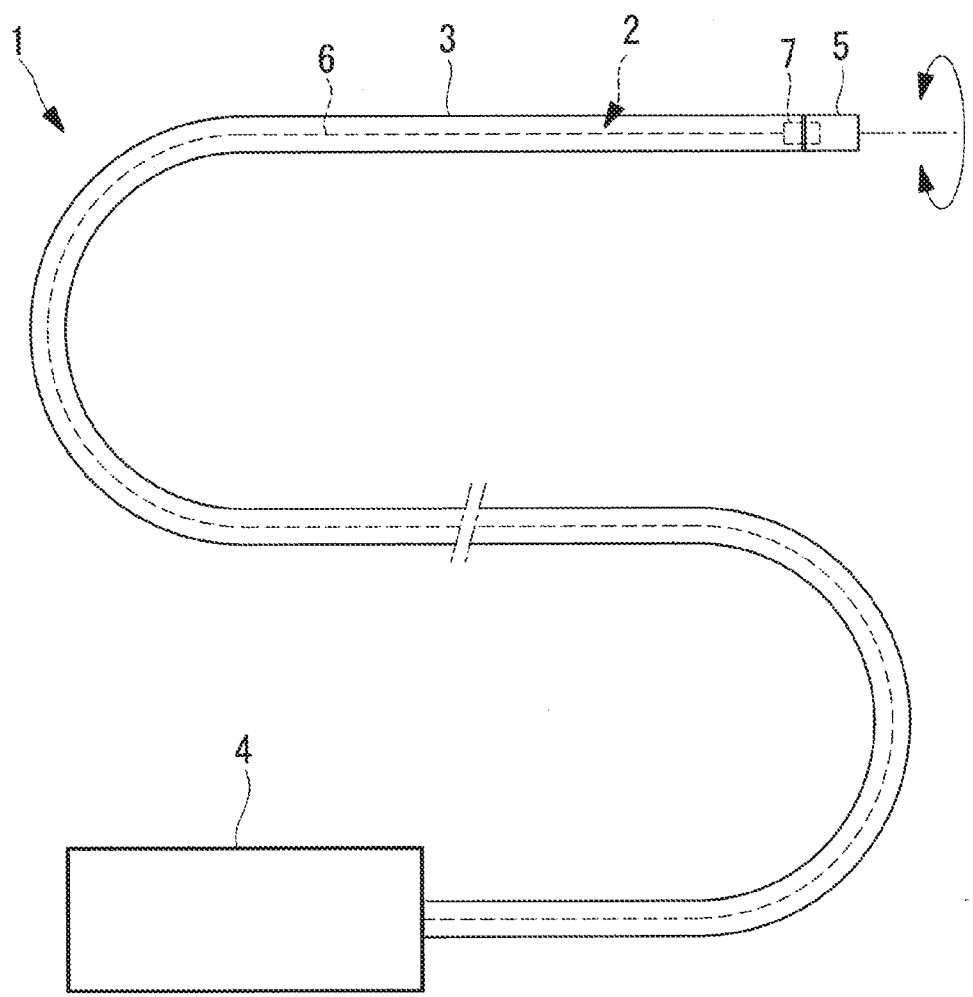
FIG. 1 is a view showing the overall configuration of a medical device according to an embodiment of the present invention.

As shown in FIG. 1, the medical device 1 of this embodiment is provided with: an elongated tubular flexible insertion portion 3; an operation unit 4 that is fixed at the proximal end of the insertion portion 3 and that is operated by a user; a rotation unit 5 that is supported, at the distal end of the insertion portion 3, in a rotatable manner about the longitudinal axis of the insertion portion 3; and the medical-device force transmission mechanism 2 of this embodiment, which transmits a force applied to the operation unit 4 to the rotation unit 5 to rotate the rotation unit 5.

The operation unit 4 is provided with: a handle (not shown) that is gripped by the user; and a lever (not shown) that is moved with respect to the handle, thereby applying tension to a wire 6 in the medical-device force transmission mechanism 2.

The medical-device force transmission mechanism 2 of this embodiment is provided with: the single wire (tension transmitting member, first force transmitting part) 6, of which the ends are respectively connected to the lever and to which tension is respectively applied through movement of the lever; a pulley (force converting part) 7 that is disposed in the vicinity of the distal end of the insertion portion 3 and that converts the tension of the wire 6 into a rotational force about an axis parallel to the longitudinal axis of the insertion portion 3; and a pair of gears (second force transmitting part) 8a and 8b that transmit the rotational force of the pulley 7 to the rotation unit 5 to rotate the rotation unit 5.

Figure 2:
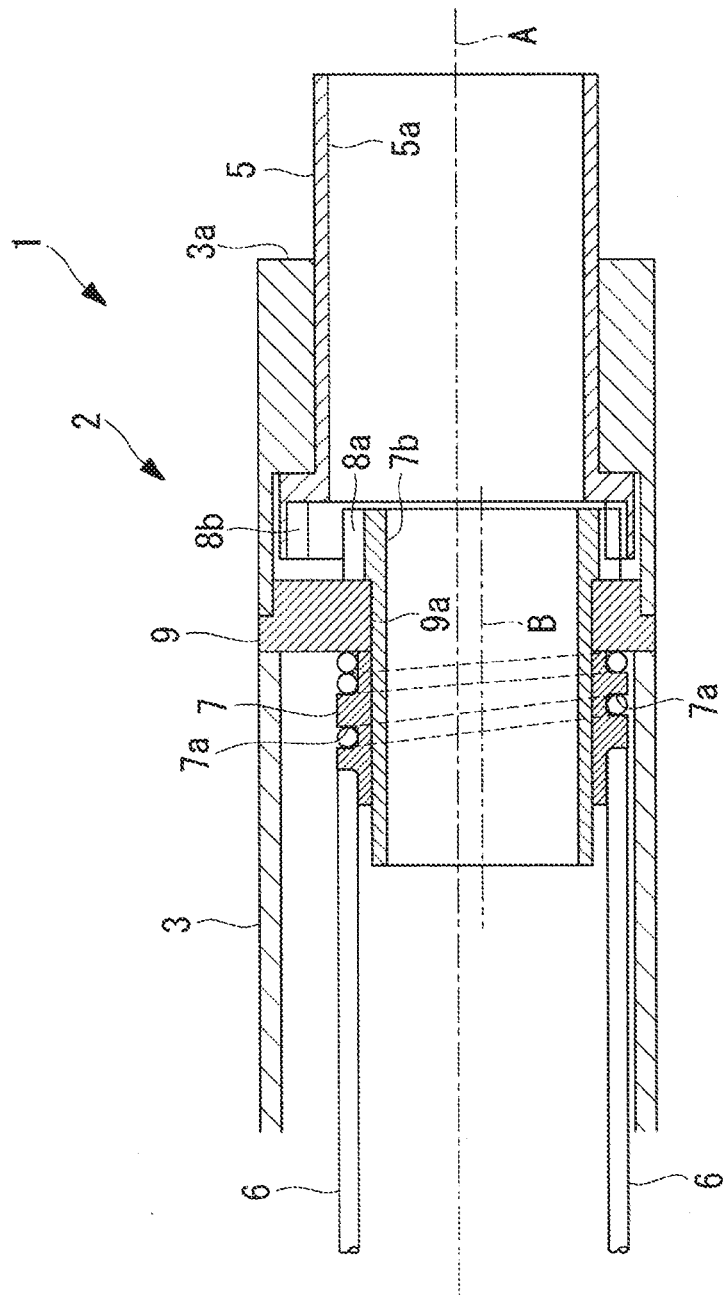
FIG. 2 is a longitudinal sectional view showing a medical-device force transmission mechanism according to the embodiment of the present invention, provided in the medical device shown in FIG. 1.

As shown in FIG. 2, the insertion portion 3 has, at the distal end thereof, a cylindrical section 3a into which the rotation unit 5 is rotatably fitted. The rotation unit 5 is formed into a cylindrical shape having a through-hole 5a at the center.

As shown in FIG. 2, the pulley 7 has a spiral groove 7a on the outer peripheral surface, so that a middle section of the wire 6 is wound along the groove 7a. Accordingly, it is possible to rotate the pulley 7 in one direction by applying a tension to one of the wire 6 extending from the pulley 7 and to rotate the pulley 7 in the other direction by applying a tension to the other wire 6 extending from the pulley 7.

The pulley 7 is also formed into a cylindrical shape having a through-hole 7b at the center. A bracket 9 is fixed in the vicinity of the distal end of the insertion portion 3, and the bracket 9 is provided with a fitting hole 9a that is eccentric with respect to the longitudinal axis of the insertion portion 3. The outer peripheral surface of the pulley 7 is partially fitted into the fitting hole 9a, which is provided in the bracket 9, thereby being supported in a rotatable manner about an axis B parallel to a central axis A of the rotation unit 5.

Figure 3:
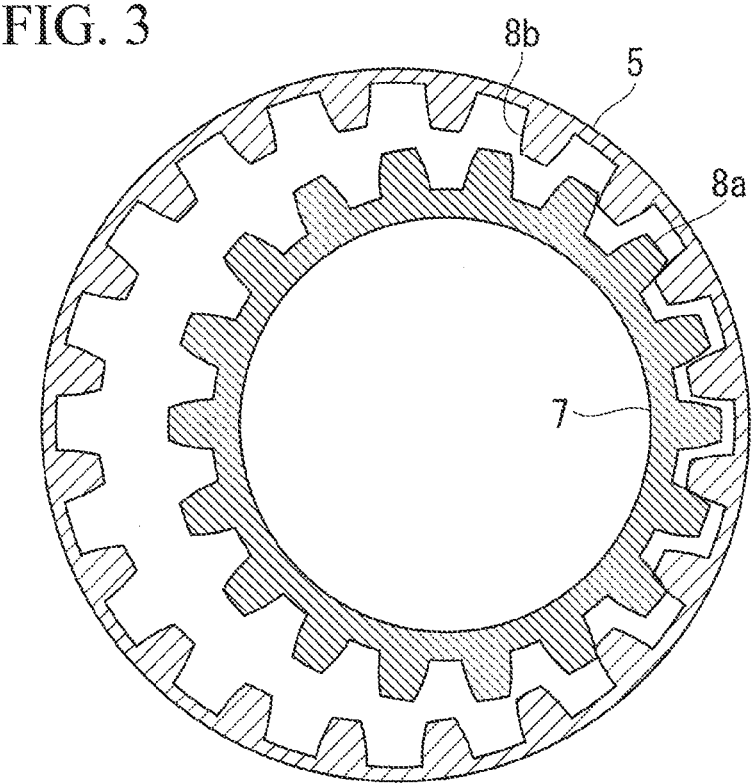
FIG. 3 is a view showing a second force transmitting part provided in the medical-device force transmission mechanism shown in FIG. 2.

As shown in FIG. 3, the pair of gears 8a and 8b are constituted of: a drive gear 8a that is an external gear fixed on the distal end of the pulley 7; and a driven gear 8b that is an internal gear provided on an inner surface of the rotation unit 5. The number of teeth of the drive gear 8a is less than the number of teeth of the driven gear 8b, so that the rotational speed of the drive gear 8a is reduced and is transmitted to the driven gear 8b.

The operation of the thus-configured medical device 1 and medical-device force transmission mechanism 2 of this embodiment will be described below.

According to the medical-device force transmission mechanism 2 of this embodiment, when the user grips the handle of the operation unit 4 and moves the lever in one direction, a tension is applied to one of the wire 6, which is fixed to the lever, and the tension is transmitted to the vicinity of the distal end of the insertion portion 3 by the wire 6, which passes through the insertion portion 3.

The pulley 7, which is provided at the distal end of the insertion portion 3 and around which the wire 6 is wound, is rotated in the one direction by means of the tension transmitted by the wire 6. Accordingly, the pulley 7 converts the tension into a rotational force. As shown in FIGS. 2 and 3, because the drive gear 8a is fixed to the pulley 7, the driven gear 8b is engaged with the drive gear 8a, and the driven gear 8b is provided on the rotation unit 5, the rotational force converted by the pulley 7 is transmitted from the drive gear 8a to the driven gear 8b, thus rotating the rotation unit 5 in the one direction.

Furthermore, when the lever is moved in the other direction, a tension is applied to the other wire 6, which is fixed to the lever, thus rotating the rotation unit 5 in the other direction.

In this case, according to the medical-device force transmission mechanism 2 of this embodiment, the tension is transmitted by the wire 6, unlike a conventional mechanism in which a rotational force itself is transmitted by a drive shaft along the longitudinal direction of the insertion portion 3; therefore, even when the flexible insertion portion 3 is curved, thus increasing the friction force between the wire 6 and the insertion portion 3, it is possible to reduce the influence of the friction, compared with that of the drive shaft for transmitting the rotational force itself.

Furthermore, because the rotational force converted by the pulley 7 is increased through deceleration on the basis of the gear ratio of the drive gear 8a and the driven gear 8b and is transmitted to the rotation unit 5, there is an advantage in that a large rotational force can be generated in the rotation unit 5, with a small tension.

As a result, through the operation of the operation unit 4, it is possible to reduce the influence of the friction and to smoothly rotate the rotation unit 5. Accordingly, there is an advantage in that various types of treatment part fixed to the rotation unit 5 can be rotated smoothly.

Furthermore, deceleration is achieved by the pair of gears 8a and 8b, thereby making it possible to increase the amount of traction of the wire 6 with respect to the rotational speed of the rotation unit 5, compared with a case in which the gear ratio is 1. Specifically, it is necessary to significantly pull the wire 6 in order to rotate the rotation unit 5 only by a small angle, and thus, there is an advantage in that the rotation of the rotation unit 5 can be finely adjusted.

Furthermore, in this embodiment, because the pulley 7 is rotatably supported at a position eccentric in one direction with respect to the central axis of the insertion portion 3, the pulley 7 is biased, thereby making it possible to increase the space at one side in the circumferential direction of the pulley 7. Accordingly, it is possible to facilitate routing of the wire 6 to be wound around the pulley 7 and to prevent the wire 6 from being excessively curved.

Furthermore, in this embodiment, because the pulley 7 and the rotation unit 5 have the through-holes 7b and 5a at the centers thereof, it is possible to ensure a power transmission path to the treatment tool, such as grasping forceps or an electric cautery, fixed to the rotation unit 5.

Figure 4:
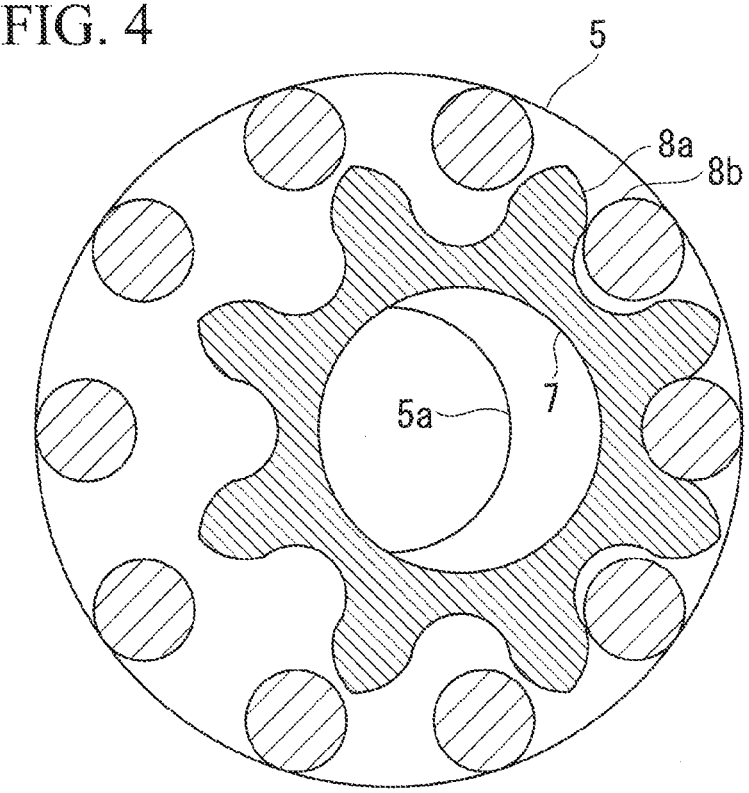
FIG. 4 is a view showing a modification of a second force transmitting part.

Note that, in this embodiment, although the pair of gears constituted of the drive gear 8a and the driven gear 8b, which are engaged with each other, is shown as an example of the second force transmitting part, it is also possible to adopt a pin gear as the driven gear 8b, as shown in FIG. 4, instead of the internal gears. Accordingly, it is possible to easily configure the teeth of the driven gear 8b provided on the rotation unit 5 and to achieve a reduction in the diameters of the rotation unit 5 and the insertion portion 3.

Furthermore, although a description has been given of a case in which the rotational force is transmitted by the pair of gears 8a and 8b, the present invention is not limited thereto, and it is also possible to adopt drive rollers (not shown) and driven rollers (not shown) for transmitting the rotational force by means of friction or a viscous fluid that intervening therebetween.

Figure 5:
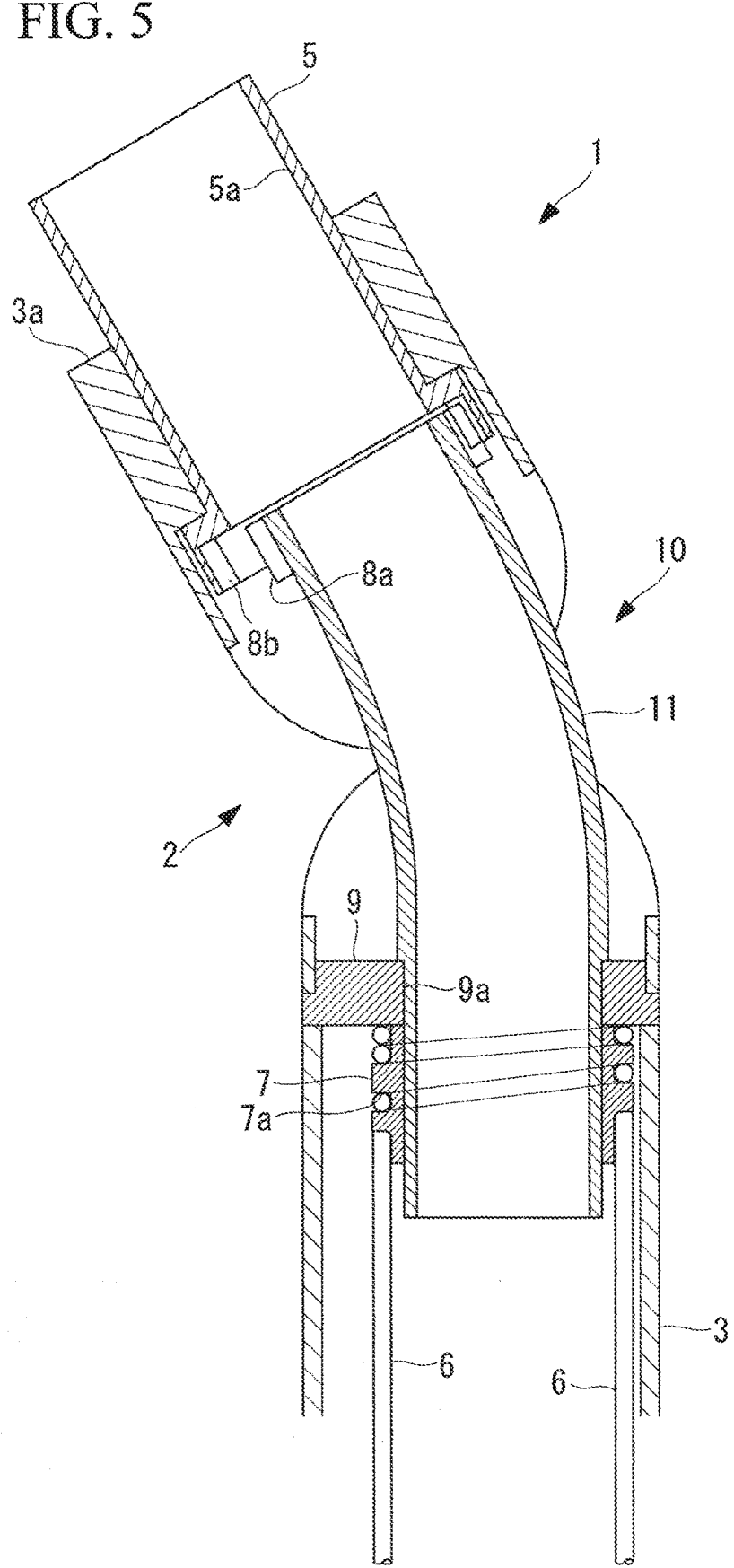
FIG. 5 is a longitudinal sectional view showing a modification of the medical-device force transmission mechanism shown in FIG. 2.

Furthermore, in the medical device 1 of this embodiment, as shown in FIG. 5, a bending joint 10 that can be bent about an axis perpendicular to the longitudinal axis of the insertion portion 3 may be provided at the distal end of the insertion portion 3.

Then, as the medical-device force transmission mechanism 2 that has the bending joint 10, it is also possible to dispose the pulley 7, which constitutes the force converting part, at a position closer to the proximal end than the bending joint 10 is and to couple the pulley 7 and the drive gear 8a by means of a flexible torque tube (drive shaft, second force transmitting part) 11.

By doing so, although the torque tube 11 is curved by the action of the bending joint 10, because the curving of the torque tube 11 is limited to a short path in which the torque tube 11 passes through the bending joint 10, the rotational force of the pulley 7 can be transmitted to the drive gear 8a without being largely affected by the influence of the friction. Furthermore, by disposing the pulley 7 at a position closer to the proximal end than the bending joint 10 is, it is possible to ensure a larger diameter of the insertion portion 3 at the proximal end of the bending joint 10 than the diameters of the bending joint 10 and the distal side of the bending joint 10, and a wide space around the pulley 7 for routing the wire 6 is ensured.

Furthermore, in the medical device 1 of this embodiment, the operation unit 4 may be driven by using an electronic device such as a motor.

Furthermore, in the medical device 1 of this embodiment, the operation unit 4 need not be fixed to the insertion portion 3. In such case, a driving-force input device is fixed to the insertion portion 3, and the driving-force input device is operated in response to a value input by the user using the operation unit 4.

Furthermore, the shape of the operation unit 4 does not need to use a handle or a lever.

From the above-described embodiments, the following aspects of the present disclosure are derived.

According to one aspect, the present disclosure provides a force transmission mechanism for a medical device, which transmits a force that is input at a proximal end of an insertion portion to be inserted into a body to a rotation unit that is supported at a distal end of the insertion portion in a rotatable manner about a longitudinal axis of the insertion portion, the force input at the proximal end being one along the longitudinal direction of the proximal end of the insertion portion, the medical-device force transmission mechanism comprising: a first force transmitting part configured to pass through an inside of the insertion portion and transmit the force to the distal end of the insertion portion; a force converting part that is disposed at the distal end of the insertion portion and configured to convert the force transmitted by the first force transmitting part into a rotational force; and a second force transmitting part configured to transmit the rotational force converted by the force converting part to the rotation unit at a different rotational speed.

According to this aspect, when a force along the longitudinal direction of the insertion portion is input at the proximal end of the insertion portion, the input force is transmitted, through the insertion portion, to the vicinity of the distal end by the first force transmitting part and is converted into a rotational force by the force converting part, which is provided in the vicinity of the distal end of the insertion portion. The converted rotational force is transmitted to the rotation unit, which is rotatably supported at the distal end of the insertion portion, at a different rotational speed by the second force transmitting part.

When the insertion portion is curved, because the force along the longitudinal direction of the insertion portion is transmitted by the first force transmitting part, which passes through the insertion portion, the force can be transmitted to the force converting part without being significantly affected by the influence of the friction, compared with a case in which the torque is transmitted by using a drive shaft. Then, transmission of the rotational force from the force converting part, which is disposed in the vicinity of the distal end of the insertion portion, to the rotation unit performed by the second force transmitting part is not affected by the friction because the transmission path is short. As a result, the rotation unit, which is disposed at the distal end of the insertion portion, can be smoothly rotated by the force input at the proximal end of the insertion portion.

In the above-described aspect, the second force transmitting part may increase, through deceleration, the rotational force converted by the force converting part and transmit the increased rotational force to the rotation unit.

By doing so, the rotational force converted by the force converting part is increased through deceleration by the second force transmitting part, and the rotation unit is rotated at a smaller rotational speed than the output of the force converting part. Accordingly, even when the force input at the proximal end of the insertion portion is small, the rotation unit can be rotated by a large rotational force. Furthermore, in order to rotate the rotation unit one turn, the output of the force converting part needs to be rotated by more than one turn, and thus, it is possible to reduce the influence of the friction to smoothly rotate the rotation unit.

Furthermore, in the above-described aspect, a bending joint may be provided at the distal end of the insertion portion and allow a rotation axis of the rotation unit to swing about an axis perpendicular to the rotation axis; the force converting part may be disposed between the proximal end of the insertion portion and the proximal end of the bending joint; and the second force transmitting part may be provided with a flexible drive shaft, configured to pass through the bending joint, and transmit the rotational force.

By doing so, it is possible to ensure a more sufficient installation space for the force converting part at the proximal end of the bending joint than at the distal end thereof, and to effortlessly convert the force along the longitudinal direction of the insertion portion into the rotational force, in particular, in a case in which the insertion portion has a small diameter. Then, the converted rotational force is transmitted, through the bending joint by the drive shaft, in a short path to the rotation unit. The transmission path used by the drive shaft is shortened, thereby making it possible to reduce the influence of the friction.

Furthermore, in the above-described aspect, the second force transmitting part may be provided with: a drive gear that is rotated by the rotational force converted by the force converting part; and a driven gear that is fixed to the rotation unit and that is engaged with the drive gear.

By doing so, engagement between the drive gear and the driven gear facilitates transmission of the rotational force at a different rotational speed.

Furthermore, in the above-described aspect, the driven gear may be a pin gear.

By doing so, with the pin gear of a simple structure, the driven gear can be configured even in a rotation unit that has an extremely small diameter.

Furthermore, in the above-described aspect, the second force transmitting part may be provided with: a drive roller that is rotated by the rotational force converted by the force converting part; and a driven roller that is fixed to the rotation unit and that is rotated by the friction with respect to the drive rollers.

By doing so, the friction between the drive roller and the driven roller facilitates transmission of the rotational force at a different rotational speed.

Furthermore, in the above-described aspect, the first force transmitting part may be an elongated tension transmitting member configured to transmit tension; and the force converting part may be a pulley around which the tension transmitting member is wound and which is rotated by the tension transmitted by the tension transmitting member.

By doing so, tension applied to the tension transmitting member at the proximal end of the insertion portion is transmitted, by the tension transmitting member, through the insertion portion to the force converting part in the vicinity of the distal end, and the pulley, around which the tension transmitting member is wound and which is rotated by the tension, thereby making it possible to easily convert the tension into the rotational force in the pulley.

Furthermore, in the above-described aspect, the pulley may have a spiral groove into which the tension transmitting member is wound, and may be supported in a rotatable manner about an axis parallel to the rotation axis of the rotation unit.

By doing so, it is possible to directly convert the tension of the tension transmitting member into a rotational force about an axis parallel to the rotation axis of the rotation unit and to smoothly rotate the rotation unit by the second force transmitting part, which is formed of simple gears or rollers.

Furthermore, in the above-described aspect, the rotation unit and the pulley may have through-holes passing therethrough in a direction along the rotation axis.

By doing so, a treatment tool, such as grasping forceps or an electric cautery, is fixed to the rotation unit, and a power transmission path to the treatment tool can be ensured by means of the through-holes of the rotation unit and the pulley.

Furthermore, according to another aspect, the present disclosure provides a medical device comprising: any one of the above-described force transmission mechanisms for medical-device; the flexible elongated insertion portion; an operation unit that is provided at the proximal end of the insertion portion and with which the force along the longitudinal direction of the insertion portion is input; and the rotation unit that is supported at the distal end of the insertion portion in a rotatable manner about the longitudinal axis of the insertion portion.

According to this aspect, when a force along the longitudinal direction of the insertion portion is input to the operation unit, the input force is transmitted to the distal end of the insertion portion by the medical-device force transmission mechanism, thus rotating the rotation unit. Even when the flexible insertion portion is curved, the influence of the friction at the insertion portion is reduced, thereby making it possible to smoothly rotate the rotation unit and to perform a smooth treatment by using a treatment part attached to the rotation unit.

According to the aforementioned aspects, an advantageous effect is afforded in that it is possible to smoothly rotate a rotation unit that is disposed at the distal end of an insertion portion and that is rotated about the longitudinal axis of the insertion portion.

REFERENCE SIGNS LIST 1 medical device
2 force transmission mechanism for medical-device
3 insertion portion
4 operation unit
5 rotation unit
5a, 7b through-hole
6 wire (tension transmitting member, first force transmitting part)
7 pulley (force converting part)
7a groove
8a drive gear (second force transmitting part)
8b driven gear (second force transmitting part)
10 bending joint
11 torque tube (drive shaft, second force transmitting part)

The invention claimed is:

1. A medical device comprising:
a tubular insertion portion;
a rotation unit provided at a distal end of the insertion portion, the rotation unit being rotatable about a longitudinal axis of the insertion portion;
an operation unit disposed at a proximal end the insertion portion,
an external gear disposed proximally to the rotation unit, the external gear having first gear teeth disposed on an outer circumferential surface; and
an internal gear engaged with the external gear, the internal gear being connected to the rotation unit, the internal gear having second gear teeth disposed on an inner circumferential surface;
wherein a force from the operation unit is transmitted to rotate the external gear, a first rotational force transmitted by the external gear is transmitted to the internal gear, and a second rotational force transmitted by the internal gear is transmitted to the rotation unit to rotate the rotation unit;
the external gear and the internal gear each having an opening extending in a longitudinal axis direction such that the insertion portion in at least a portion corresponding to the external gear and the internal gear is hollow in the longitudinal axis direction;
a number of the second gear teeth of the internal gear is greater than a number of the first gear teeth of the external gear, and
the second rotational force transmitted to the rotation unit by the internal gear is increased relative to the first rotational force based on a gear ratio of the external gear and the internal gear.

* * * * *